United States Patent [19]

de Villiers et al.

[11] Patent Number: 5,187,090

[45] Date of Patent: Feb. 16, 1993

[54] HUMAN PAPILLOMA VIRUS TYPE 57 AND THE DNA THEREOF

[75] Inventors: Ethel-Michele de Villiers, Hirschberg; Anja Hirsch-Behnam; Harald zur Hausen, both of Heidelberg, all of Fed. Rep. of Germany

[73] Assignee: Behringwerke Aktiengesellschaft, Marburg, Fed. Rep. of Germany

[21] Appl. No.: 389,807

[22] Filed: Aug. 4, 1989

[30] Foreign Application Priority Data

Aug. 6, 1988 [DE] Fed. Rep. of Germany ....... 3826793

[51] Int. Cl.⁵ .................. C12N 7/00; C12N 15/37; C12Q 1/70
[52] U.S. Cl. ..................... 435/235.1; 536/23.72; 435/5
[58] Field of Search ...................... 435/235.1, 5, 172.3, 435/239; 536/27

[56] References Cited

PUBLICATIONS

De Villiers 1989, *J. Virology* vol. 63 pp. 4898–4903.
De Villiers, E-M. et al. 1989. *Virology*, vol. 171p. 248–253.
Shah, K. 1985. In *Virology*, ed. B. N. Fields et al, pp. 371–391.
Kremsdorf, D. et al. 1983. *J. Virol.* vol. 48 pp. 340–351.
Kremsdorf,- D. et al. 1984. *J. Virol.* vol. 52 pp. 1013–1018.
Dürst, M. et al. 1985. *J. Gen. Virol.* vol. 66 pp. 1515–1522.
L. Gissman et al., Inc. J. Cancer 29:143–146 (1982).
C. Yanisch-Perron et al., Gene 33:103–119 (1985).
T. Maniatis et al., Molecular Cloning: A Laboratory manual: Cold Spring Harbor Laboratory Press, New York (1982), Table of Contents.
J. Messing et al., Proc. Natl. Acad. Sci. USA 74:3642–3646 (1977).
H. C. Birnboim and J. Doly, Nucl. Acids Res 7:1513–1523 (1979).
E. M. Southern, J. Mol. Biol. 98:503–517 (1975).
S. T. Cole and O. Danos, J. Mol. Biol. 193:599–608 (1987).

*Primary Examiner*—Douglas W. Robinson
*Assistant Examiner*—Mary E. Mosher
*Attorney, Agent, or Firm*—Finnegan, Henderson, Farabow, Garrett and Dunner

[57] ABSTRACT

The invention describes the isolation for the first time of human papilloma virus (HPV) 57, the partial characterization of its genome and its cloning in pUC 19. This opens up a way of diagnosing those tumors (oral, genital and cutaneous tumors) which are associated with HPV 57.

2 Claims, 2 Drawing Sheets

HUMAN PAPILLOMA VIRUS TYPE 57 AND THE DNA THEREOF

The human papilloma viruses (HPV) form a group of more than 50 different types. HPV has been found associated with benign (warts, condylomas in the genital region) and malignant (carcinomas of the skin and the vagina) epithelial neoplasms. Papilloma viruses cannot be grown in culture. Thus, methods of genetic manipulation are required for the use of human papilloma virus type 57 DNA (HPV 57 DNA) as a diagnostic aid and for obtaining the expression products, for using them as antigens, for isolating antibodies and for preparing corresponding diagnostic aids and therapeutic agents.

The invention is based on the isolation for the first time of HPV 57, partial characterization of its genome and cloning in pUC 19. This opens up a way of diagnosing tumors (oral, genital and cutaneous tumors) associated with HPV 57.

The invention is defined in the patent claims. Further embodiments of the invention are described in detail hereinafter.

The cloning of HPV 57 made it possible to compare with 56 other HPVs. HPV 2 and HPV 27 are very closely related, and hybridization in liquid phase revealed 17% and 25% homology, respectively. The colinearity of HPV 57 with HPV 18 was determined (FIG. 1) and a physical genome map for restriction enzyme clearages (FIG. 2) was constructed.

This has opened up a way of testing neoplasms (genital and cutaneous tumors), especially tumors on the head, for the presence of HPV 57 and, where appropriate, a therapeutic approach via antibodies to HPV 57 proteins.

EXAMPLES

1. Isolation of HPV 57 DNA

High molecular weight DNA was isolated from an inverted papilloma of the maxillary sinus as described (Gissmann et al. (1982), Int. J. Cancer 29, 143-146).

2. Cloning of HPV 57 in the plasmid pUC 19

The known plasmid pUC 19 (Yanish-Perron et al. (1985), Gene 33, 113-119) was chosen as cloning vector. HPV 57-containing cellular double-stranded DNA was cleaved with Eco RI and then cloned into pUC 19 (Maniatis et al. (1982) Molecular Cloning: A Laboratory Manual; Cold Spring Harbor Laboratory Press, New York). Recombinant clones were identified in the β-galactosidase test (Messing et al. (1977), Proc. Nat. Acad. Sci. USA 75, 3641-3646) and rapid DNA extraction was followed by analysis of DNA fragments ligated in (Birnboim, H.L. and Doly, J. (1979), Nucl. Acids. Res. 7, 1513-1523).

3. Physical genome maps of HPV 57

HPV 57 DNA detached from the vector by Eco RI cleavage was digested with restriction endonucleases and the corresponding physical genome maps were constructed by generally known methods. The result is summarized in FIG. 2, the sole Eco RI clearage site being used to linearize the HPV 57 molecule. The table shows the length of the individual restriction fragments.

4. Comparison with other HPVs

The DNA of the HPV 57 genome was compared by means of DNA/DNA hybridization under various degrees of stringency with the DNAs of 56 available HPV types (E.M. Southern (1975), J. Mol. Biol. 98, 50-517). Under high-stringency conditions (melting temperature Tm −20° C.) HPV 57 DNA hybridizes with HPV 2 and HPV 27.

Figure 1:
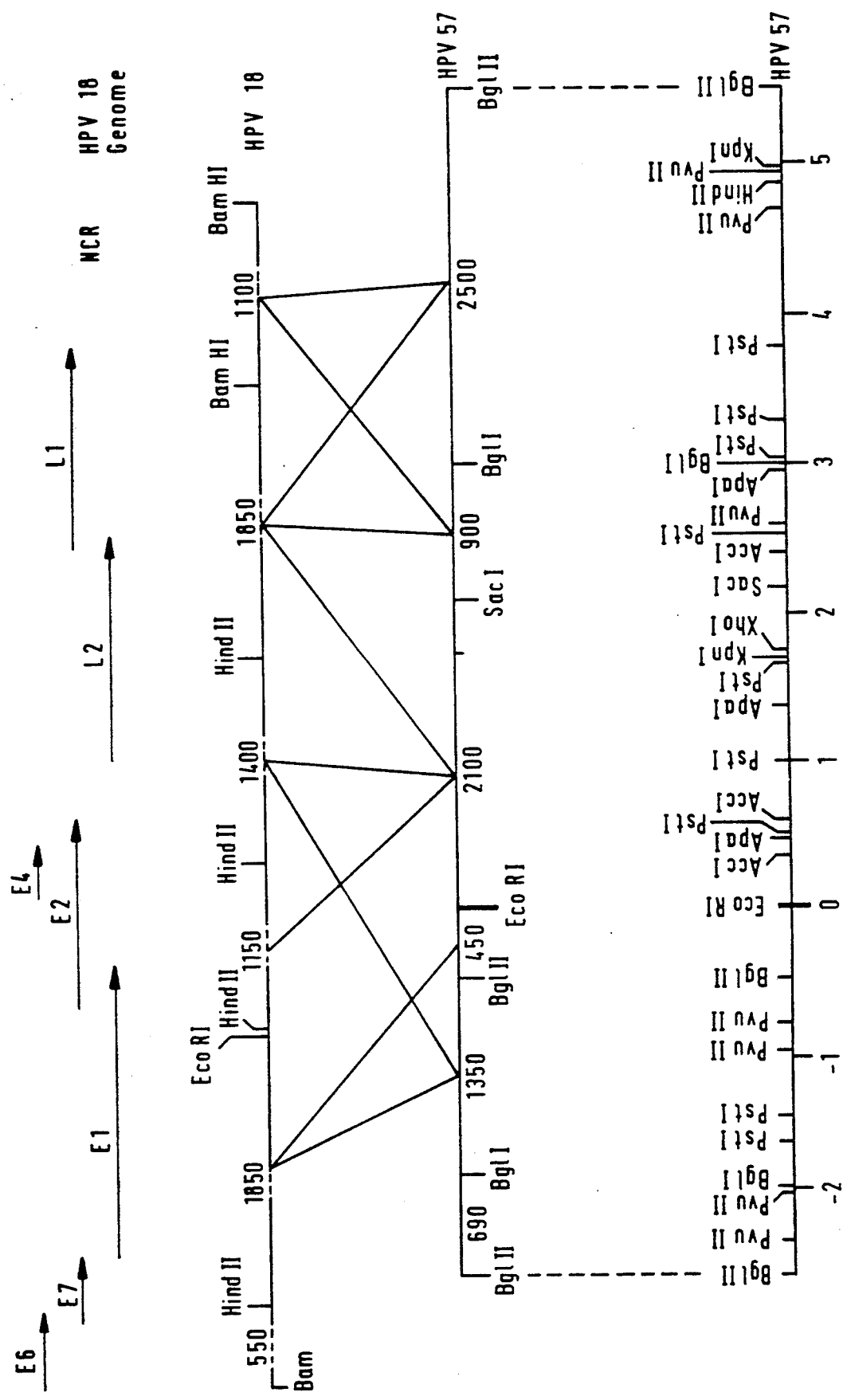
FIG. 1 Colinear alignment of HPV 57 to HPV 18 DNA.

The colinearity with HPV 18 based on hybridization experiments is shown in FIG. 1.

Knowing the HPV 18 DNA sequence (Cole et al. (1987) J. Mol. Biol. 193, 599-608) it is possible to deduce the open reading frames of HPV 57 and thus to obtain the HPV 57 proteins by general methods for subcloning with subsequent expression in prokaryotic or eukaryotic expression systems.

The pUC 19 plasmid DNA containing HPV 57 was deposited on Jun. 13, 1988, at the Deutsche Sammlung für Mikroorganismen (German Microorganism Collection) under the number DSM 4694 in accordance with the Budapest Treaty.

Figure 2:
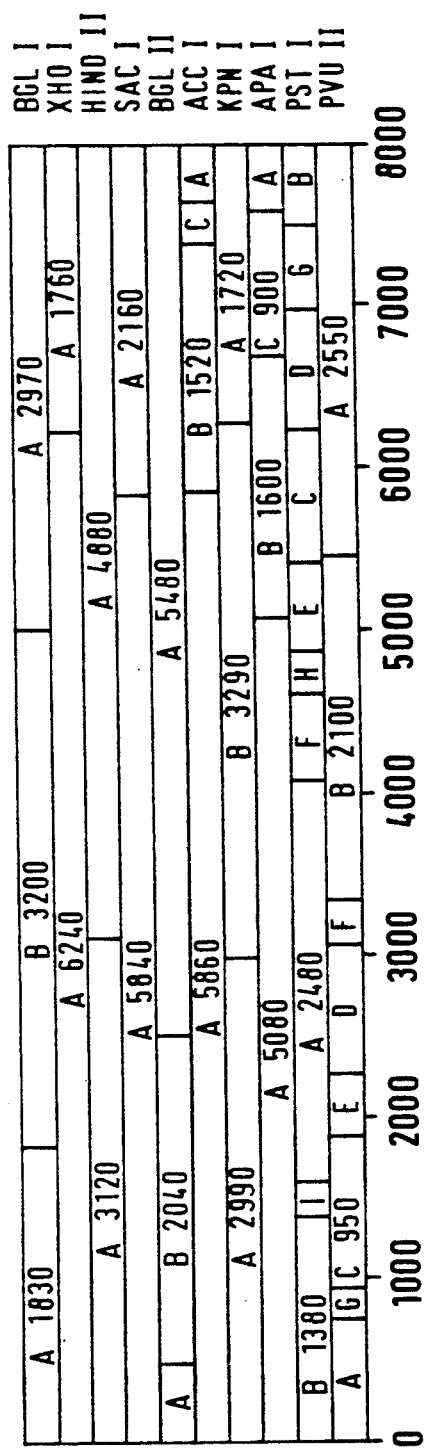
FIG. 2 Restriction enzyme analysis of HPV 57.

Key to FIG. 2

The circular genome was cloned via its Eco RI clearage site, the figures following the letters designating the fragments indicate the length in base-pairs (bp). Restriction enzymes with one cleavage site are XhoI, HindII and SacI. The restriction enzymes XbaI, SalI, BamHI, HindIII and HpaI do not cleave. The exact location of the four 500 bp-long PstI fragments was not determined.

TABLE

|   | ACC I | AFA I | DGL I | BGL II | HIND II | KPN I | PSI I | PVU II | SAC I | XHO I |
|---|-------|-------|-------|--------|---------|-------|-------|--------|-------|-------|
| A | 6.220 | 5.500 | 1.800 | 5.960  | 8.000   | 1.710 | 2.180 | 3.290  | 8.000 | 8.000 |
| B | 1.520 | 1.600 | 3.200 | 2.010  |         | 3.290 | 1.890 | 2.100  |       |       |
| C | .260  | .900  |       |        |         |       | .820  | .950   |       |       |
| D |       |       |       |        |         |       | .710  | .800   |       |       |
| E |       |       |       |        |         |       | .510  | .390   |       |       |
| F |       |       |       |        |         |       | .530  | .200   |       |       |
| G |       |       |       |        |         |       | .520  | .190   |       |       |
| H |       |       |       |        |         |       | .260  |        |       |       |
| I |       |       |       |        |         |       | .220  |        |       |       |

We claim:

1. Isolated human papilloma virus (HPV) 57 including equivalent variants thereto.

2. Isolate HPV 57 DNA including equivalent variants thereto.

UNITED STATES PATENT AND TRADEMARK OFFICE
CERTIFICATE OF CORRECTION

PATENT NO. : 5,187,090

DATED : February 16, 1993

INVENTOR(S) : Ethel-Michele de Villiers

It is certified that error appears in the above-identified patent and that said Letters Patent is hereby corrected as shown below:

Claim 2, column 2, line 64, change "Isolate" to --Isolated--.

Signed and Sealed this

Twenty-seventh Day of September, 1994

Attest:

BRUCE LEHMAN

*Attesting Officer*  *Commissioner of Patents and Trademarks*